United States Patent [19]

Adams et al.

[11] Patent Number: 5,439,482
[45] Date of Patent: Aug. 8, 1995

[54] PROPHYLACTIC IMPLANTABLE CARDIOVERTER-DEFIBRILLATOR

[75] Inventors: Theodore P. Adams, Edina; Mark W. Kroll, Minnetonka, both of Minn.

[73] Assignee: Angeion Corporation, Plymouth, Minn.

[21] Appl. No.: 126,044

[22] Filed: Sep. 23, 1993

Related U.S. Application Data

[63] Continuation-in-part of Ser. No. 864,789, Apr. 7, 1992, abandoned, Ser. No. 33,632, Mar. 16, 1993, abandoned, Ser. No. 108,130, Aug. 16, 1993, and Ser. No. 125,288, Sep. 22, 1993.

[51] Int. Cl.$^6$ .............................. A61N 1/39
[52] U.S. Cl. .......................... 607/5; 607/36
[58] Field of Search ........................ 607/5, 7, 36

[56] References Cited

U.S. PATENT DOCUMENTS

| | | | |
|---|---|---|---|
| 3,926,198 | 12/1975 | Kolenik | 607/36 |
| 4,013,081 | 12/1977 | Kolenik | 607/36 |
| 4,800,883 | 1/1989 | Winstrom | 607/7 |
| 5,235,979 | 8/1993 | Adams | 607/5 |
| 5,241,960 | 9/1993 | Anderson et al. | 607/5 |

OTHER PUBLICATIONS

Schuder et al "Experimental Ventricular Defibrillation with an Automatic and Completely Implanted System" vol. XVI Trans Amer Soc Artif Int Organs, 1970.
"Cardiac Shocks: Space Age Help for the Heart" Time, p. 49, 18 Aug. 1980.
Winkle et al "Practical Aspects of automatic cardioverter/defibrillator implantation" Progress in Cardiology pp. 1335–1346, Nov. 1984.
Zipes et al "Early Experience with an Implantable Cardioverter", The New England Journal of Medicine, pp. 485–489, 23 Aug. 1984.

*Primary Examiner*—Lee S. Cohen
*Assistant Examiner*—Marianne Parker
*Attorney, Agent, or Firm*—Patterson & Keough

[57] ABSTRACT

A practical and effective prophylactic implantable cardioverter defibrillator (ICD) that has the potential to benefit a large number of patients with less severe cardiac conditions who now lack the opportunity to be served in a practical way by existing ICD systems. Unlike existing ICD systems, the prophylactic ICD is designed to deliver between about 100 to 200 shocks, with each shock having a maximum delivered energy value of only about 25 joules. As a result, the initial stored energy requirements of the prophylactic ICD system are less than about 12,000 joules, and both the battery and the capacitor systems can be significantly smaller than existing ICD system. The smaller battery and capacitor systems produce in an implantable device having a physical size small enough to permit implantation of the device in the pectoral region. By using the particular ranges of number of shocks and maximum energy value for each shock to design the ICD system, the result is a practical prophylactic ICD system that will provide effective prophylactic therapy for prospective cardiac incidents in patients with less severe cardiac conditions.

24 Claims, 3 Drawing Sheets

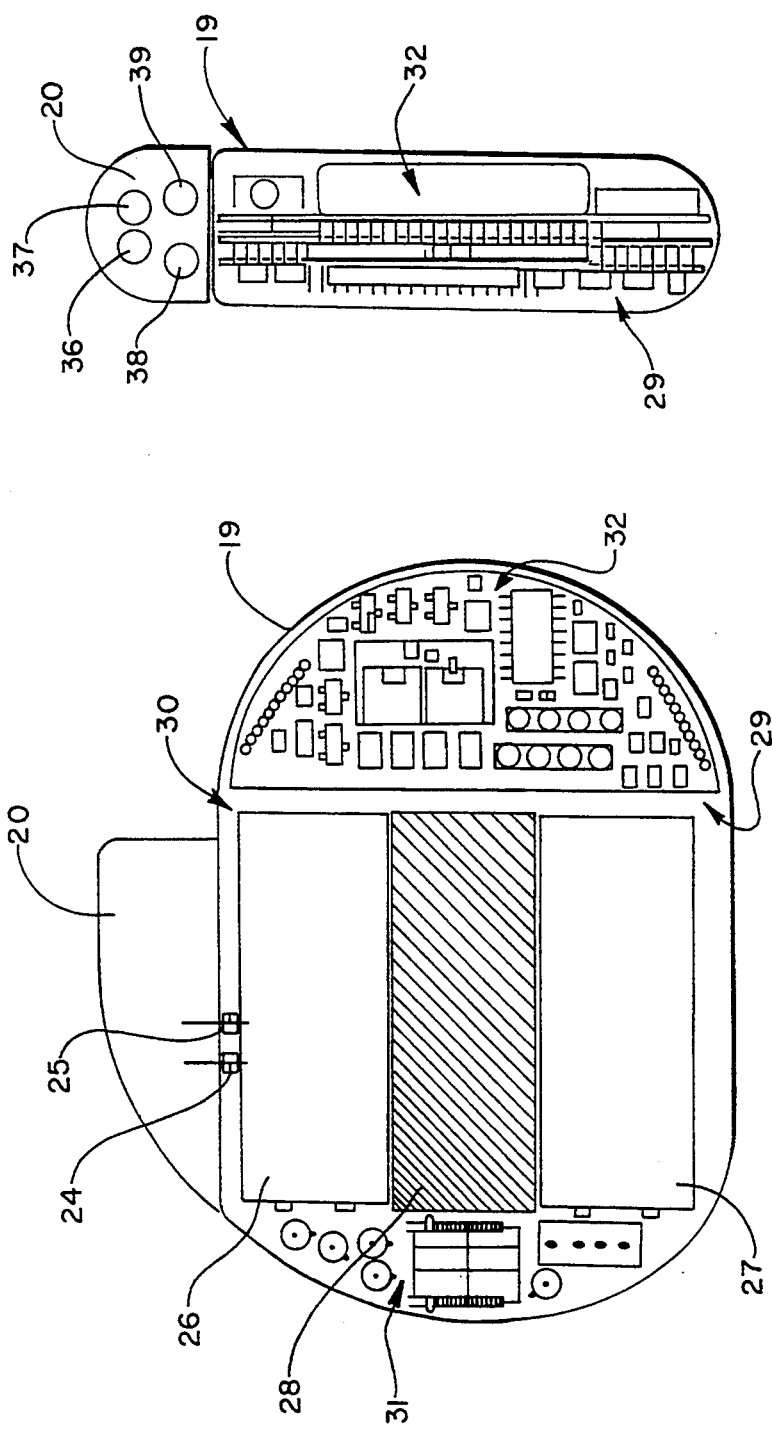

PROPHYLACTIC IMPLANTABLE CARDIOVERTER-DEFIBRILLATOR

This application is a continuation-in-part application of four prior applications filed in the United States Patent and Trademark Office, the first of which was filed on Apr. 7, 1992 and entitled PROPHYLACTIC IMPLANTABLE CARDIOVERTER-DEFIBRILLATOR, now abandoned, Ser. No. 07/864,789, the second of which was filed on Mar. 16, 1993 and entitled IMPLANTABLE CARDIOVERTER DEFIBRILLATOR HAVING A SMALLER DISPLACEMENT VOLUME, now abandoned, Ser. No. 08/033,632, the third of which was filed on Aug. 16, 1993 and entitled IMPROVED DUAL BATTERY POWER SUPPLY FOR AN IMPLANTABLE CARDIOVERTER DEFIBRILLATOR, Ser. No. 08/108,130 and the fourth of which was filed on Sep. 22, 1993 and entitled OVERCHARGED FINAL COUNTERSHOCK FOR AN IMPLANTABLE DEFIBRILLATOR, Ser. No. 08/125,288, all of which are assigned to the assignee of the present invention and the disclosure of each of which is hereby incorporated in the present application.

BACKGROUND OF THE INVENTION

1. Field of the Invention

The present invention relates generally to implantable cardioverter-defibrillator (ICD) systems, and more particularly, to a prophylactic or preventive ICD system.

2. Background Information

Little effort has been expended in developing ICDs for people having only mildly abnormal cardiac conditions. Virtually all existing ICD systems are designed for people with severely abnormal hearts, and hence, these ICD systems have been used for lifesaving intervention in crisis situations. Such ICD systems, for a substantial number of reasons, are unsuited for use by patients whose need is for less severe treatment, and for protective intervention at most.

One factor which distinguishes the use of ICD systems as a treatment therapy, rather than a prophylactic therapy, relates to the criteria embodied in the ICD system that determine when an electrical shock should be administered. Although substantial progress is being made currently in devising and developing more accurate methods for identifying tachycardias and fibrillations, uncertainties remain. Hence, it is necessary to provide a detection "guard band" or to acknowledge a range of uncertainty in relation to the appropriateness of shock delivery. When the ICD system is used as treatment therapy for immediate lifesaving purposes, the criterion used to determine when an electrical shock should be delivered can lead to the delivery of a number of "false-positive" shocks, even when the patient does not necessarily require shock therapy. A false-positive shock administration is painful and disconcerting to the patient, and potentially hazardous as well, however, delivery of a false-positive shock is preferred to the alternative of overlooking a true cardiac crisis that might not otherwise be detected due to the uncertainty of existing detection criterion.

Other factors which distinguish the use of an ICD system as a treatment therapy for an existing severe cardiac condition, rather than as a prophylactic therapy for a prospective cardiac incident, involve the number of shocks that the ICD system must be designed to be able to deliver during its implanted life and the energy of these delivered shocks.

All of the existing ICD systems which have been approved by the Federal Drug Administration (FDA) require that the ICD system be capable of delivering at least 250 shocks and up to 400 shocks, each shock having a maximum stored energy value of between 34 to 40 joules. Together with the energy required for cardiac monitoring over the lifetime of the device, these requirements dictate that the ICD system must have initial stored energy requirements of at least 15,000 to 20,000 joules or more. Both of these factors directly affect the physical size of the ICD system due to the dominance of the battery and the discharge capacitor in determining the physical volume of the ICD system package. The size of the ICD system, in turn, affects possible implantation sites. As a result, all of the existing ICD systems approved by the FDA are larger than about 120 cc and require implantation in the relatively spacious abdominal cavity. In order to obtain effective current distribution for a defibrillation shock when implanted in the abdominal cavity, existing ICD systems often must use patch electrodes that require transthoracic implantation. In contrast, implantable pacemakers, for example, are much smaller in volume and can be preferably implanted in the pectoral region and are connected to the heart by transvenous catheters, thereby simplifying the implantation procedure. Not surprisingly, the larger ICD systems are also more costly, and this too, limits their utility in prophylactic applications.

A number of studies have been initiated to determine the viability of using existing ICD systems for prophylactic purposes. Nisam, S. et al. "Identifying patients for prophylactic automatic implantable cardioverter defibrillator therapy: Status of prospective studies", *Am Heart J*, 1991; 122:607–612; MADIT Executive Committee. "Multicenter Automatic Defibrillator Implantation Trial (MADIT): Design and Clinical Protocol", PACE, 1991; 14:920–927; Moss, A., "Prospective Antiarrhythmia Studies Assessing Prophylactic Pharmacological and Device Therapy in High Risk Coronary Patients", PACE, 1992, 15:694–96; and Kuck, K. et al, "Prospective Studies Assessing Prophylactic Therapy in High Risk Patients: The German Dilated CardioMyopathy Study (GDCMS)—Study Design", PACE, 1992, 15:697–700. In all of these studies, however, existing ICD systems are being used and there are no suggestions to how to design a prophylactic ICD system.

The need for a prophylactic implantable cardioverter defibrillator has long been recognized by the medical community, but there presently is no agreement on how such a device should be designed. While many of the issues might appear at first to be relatively simple design choices, cardiac experts cannot decide on how a prophylactic ICD system should be implanted, what therapies it should offer, how much the device should cost, or how many shocks the device will need to be able to deliver. Hauser, R., "Attributes of a Prophylactic Implantable Cardioverter Defibrillator: How Close Are We?", PACE, Vol. 16 (Mar. 1993), pp. 582–85.

In his article, for example, Dr. Hauser directly addresses the issue of the number of shocks required of a prophylactic ICD device. "Another question is the number of shocks a PAICD [prophylactic automatic implantable cardioverter defibrillator] should be capable of delivering. Experts cannot agree. The short-term goal is to rescue the patient from the initial episode and to provide defibrillation back-up until the patient can be transported to the appropriate medical facility. Are 5 or 10 or 50 shocks sufficient to accomplish this goal?. Further, what do you do with the patient after the initial event?. Replace the unit with a standard ICD?. This strategy adds not only to cost, but also to potential patient morbidity (e.g., infection related to the replacement procedure). These are important questions whose answers will profoundly affect the economics of prophylactic devices and how the medical community and society view this therapy." Id. at 583-84.

While existing ICD systems have proven effective when used as a treatment therapy for severe cardiac conditions, these devices are not adapted to meet the recognized needs of an ICD that would provide prophylactic therapy for a prospective cardiac incident in patient's with less severe cardiac conditions. In addition, while some of the goals of a prophylactic ICD systems are well known, there is simply no agreement in the medical community on how, or even if, these goals can be achieved. Accordingly, it would be desirable to provide a design for a practical prophylactic ICD system that can meet the ultimate goal of providing effective prophylactic therapy for prospective cardiac incidents in patients with less severe cardiac conditions.

SUMMARY OF THE INVENTION

The present invention provides a design for a practical and effective prophylactic implantable cardioverter defibrillator (ICD) that has the potential to benefit a large number of patients with less severe cardiac conditions who now lack the opportunity to be served in a practical way by existing ICD systems. Unlike existing ICD systems, the prophylactic ICD is designed to deliver between about 100 to 200 shocks, with each shock having a maximum delivered energy value of only about 25 joules. As a result, the initial stored energy requirements of the prophylactic ICD system are less than about 12,000 Joules, and both the battery and the capacitor systems can be significantly smaller than existing ICD system. The smaller battery and capacitor systems produce in an implantable device having a physical size small enough to permit implantation of the device in the pectoral region. By using the particular ranges of number of shocks and maximum energy value for each shock to design the ICD system, the result is a practical prophylactic ICD system that will provide effective prophylactic therapy for prospective cardiac incidents in patients with less severe cardiac conditions.

While the medical community is presently uncertain as to the number of shocks required for a prophylactic ICD system, the present invention. recognizes that reducing the number of shocks that an ICD system must be able to deliver reduces the overall energy requirement, but only to a point. Even if only a single electrical shock were needed, the battery system of an ICD system must be able to deliver sufficient current to charge the capacitor system in a few seconds. Because the charging time of a capacitor is a function of the efficiency of the charging circuitry and the voltage and current delivered by the battery system, the charge-time requirement sets an effective lower limit on total plate area in the battery required to deliver the necessary current and voltage, and hence a lower limit on battery size. For a charging time of 10 seconds, for example, it has been found that the size of a battery required to meet this charge-time requirement is capable of delivering about 100 shocks having a maximum delivered energy of about 25 Joules/shocks. While 100 shocks might not provide an adequate safety margin for patients with severe cardiac conditions, 100 to 200 shocks would be a sufficient number of shocks for the prophylactic application envisioned by the present invention for patients with less severe cardiac conditions.

The decreased size of the ICD system of the present invention allows for implantation of the device in a pectoral site, which consequently enables the present invention to be effectively used for its intended prophylactic purpose. There are at least three other significant advantages for the use of the pectoral site as an implantation site for the prophylactic ICD system of the present invention, in addition to the fact that the pectoral site is a more efficient and convenient implantation site than the abdomen. First, the pectoral site permits use of the housing itself as one electrodes in the prophylactic ICD system for shock delivery. The use of the housing as an electrode augments more conventional catheter-based cardioverter-defibrillator electrodes, and will work effectively with such electrodes because current from a shock can be routed through the heart muscle such that a substantial fraction of the heart tissue needing electrical treatment is intersected by the current. As a result, less energy is required than if only catheter-based electrodes were used to deliver the shock. Second, the only electrodes other than the housing that are required by the prophylactic ICD system are catheter-based electrodes. This avoids the need for thoracic surgery that would otherwise be necessary to attach the cardiac-patch electrodes used by existing ICD systems. Finally, the implantation procedures for the prophylactic ICD system can be modeled after the highly successful implantation procedures used for pacemaker devices.

In addition to the decreased size of the ICD system, the prophylactic ICD system of the present invention also delivers a more effective countershock therapy. It has been shown that shorter duration and lower-energy pulses afford more effective treatment than the countershock pulses that have been conventionally used. This is a consequence of implementing the concept of physiologically effective current in the ICD system so as to bring the characteristic pulse duration of the prophylactic ICD system to between approximately 3 to 4 milliseconds, a value which is closer to the innate characteristic time, or chronaxie, of the human heart (approximately 2 to 4 milliseconds), rather than the existing pulse duration values that are between 6 to 9 milliseconds. In addition, a preferred embodiment of the present invention delivers the shorter duration electrical countershock as a more efficient biphasic waveform, instead of the traditional monophasic waveform. Recent studies have shown that the use of a biphasic waveform further decreases the energy required for defibrillation by about 13-29%.

Using the concept of physiologically effective current, the optimum effective capacitance for an ICD system that has an capacitive decay time constant of about 3 to 4 milliseconds is approximately 40 to 45 microfarads. As capacitor size is at least partially a function of effective capacitance value, the lower effective capacitance of 40 to 45 microfarads, as compared to at least 120 microfarads or greater for existing ICD systems, yields a significant decrease in the required size of the capacitor system of the ICD system. To store sufficient charge in a capacitor system having this small a capacitance value, however, requires voltages larger than the typical transistor and photoflash capacitor breakdown voltages of about 800 volts. Thus, the present invention strikes a compromise of using effective capacitance values of between 40 and 100 microfarads as being optimum for the capacitor system of an ICD designed for prophylactic application.

In accordance with a first embodiment of the present invention, an implantable cardioverter defibrillator for subcutaneous positioning within the pectoral region of a human patient having electrical energy storage requirements selected so as to treat mild cardiac dysrhythmia conditions comprises: a sealed housing structure constructed of a biocompatible material and having a displacement volume of less than about 75 cc and including one or more connector ports disposed in a wall of said structure for providing electrical connections between an interior space of said structure and electrode leads in said patient; circuit means within said interior space for sensing cardiac signals received from said electrode leads and, in response to the detection of an arrhythmia in said cardiac signals, controlling delivery of one or more electrical countershocks of at least 0.5 Joules to said patient; capacitor means within said interior space for storing electrical energy to generate said electrical countershocks and having an effective capacitance of less than about 100 $\mu F$; and battery means within said interior space for providing electrical energy to said circuit means and said capacitor means and capable of charging said capacitor means in less than about 10 seconds to a maximum stored electrical charge energy of less than about 27 Joules, wherein the total amount of electrical energy stored by said battery means is less than 12,000 Joules and the budgeted number of electrical countershocks is less than about 200 over a minimum lifespan of about 5 years. Despite the lower energy requirements and smaller size of this prophylactic device, it is capable of delivering countershocks having physiologically effective current values that are essentially equivalent to those of existing conventional treatment-oriented ICD systems.

Another embodiment of the prophylactic ICD system of the present invention takes advantages of the appropriateness of lower-energy treatments for patients with less severe cardiac conditions. This embodiment of the present invention assumes that relatively healthier hearts will require less energy for defibrillation than do hearts with more serious deficiencies. Consequently, this embodiment further decrease the maximum stored energy required of the ICD system to less than about 21 Joules, while retaining the shorter duration biphasic countershock waveform. When combined with a total budgeted number of countershocks of less than about 200, the result is a still further decrease in the overall size and stored energy requirements of the ICD system such that this embodiment of the prophylactic ICD system requires less than about 7500 Joules of stored energy for countershock delivery.

In accordance with a second embodiment of the present invention, an implantable cardioverter defibrillator for subcutaneous positioning within the pectoral region of a human patient having electrical energy storage requirements selected so as to treat mild cardiac dysrhythmia conditions comprises: a sealed housing structure constructed of a biocompatible material and having a displacement volume of less than about 60 cc and including one or more connector ports disposed in a wall of said structure for providing electrical connections between an interior space of said structure and electrode leads in said patient; circuit means within said interior space for sensing cardiac signals received from said electrode leads and, in response to the detection of an arrhythmia in said cardiac signals, controlling delivery of one or more electrical countershocks of at least 0.5 Joules to said patient; capacitor means within said interior space for storing electrical energy to generate said electrical countershocks and having an effective capacitance of less than about 100 $\mu F$; and battery means within said interior space for providing electrical energy to said circuit means and said capacitor means and capable of charging said capacitor means to a maximum electrical charge energy of less than about 21 Joules, wherein the budgeted number of electrical countershocks is less than about 200 countershocks and the total amount of electrical energy stored by said battery means for shock delivery is less than about 7500 Joules.

Still another embodiment of the present invention takes advantage of shortening the minimum lifespan of the device to further decrease the overall size and stored energy requirements of the prophylactic ICD system. It has been found that the most significant risk of fibrillation in patients with less severe cardiac conditions who have experienced a heart attack (myocardial infarction) will occur within the first 12 to 24 months following the heart attack. After this period, the incidence of fibrillation decreases significantly. Accordingly, in accordance with this embodiment an even smaller prophylactic ICD system is provided by shortening the minimum lifespan of the device to about 2 to 3 years and further decreasing the size of the capacitor and battery systems of the prophylactic ICD system.

In accordance with a third embodiment of the present invention, an implantable cardioverter defibrillator for subcutaneous positioning within the pectoral region of a human patient having electrical energy storage requirements selected so as to treat mild cardiac dysrhythmia conditions for a minimum lifespan of less than about 3 years comprises: a sealed housing structure constructed of a biocompatible material and having a displacement volume of less than about 60 cc and including one or more connector ports disposed in a wall of said structure for providing electrical connections between an interior space of said structure and electrode leads in said patient; circuit means within said interior space for sensing cardiac signals received from said electrode leads and, in response to the detection of an arrhythmia in said cardiac signals, controlling delivery of one or more electrical countershocks of at least 0.5 Joules to said patient; capacitor means within said interior space for storing electrical energy to generate said electrical countershocks and having an effective capacitance of less than about 100 $\mu F$; and battery means within said interior space for providing electrical energy to said circuit means and said capacitor means, the battery means capable of charging said capacitor means to a maximum electrical charge energy of less than about 21 Joules, wherein the budgeted number of electrical countershocks is less than about 200 countershocks and the total amount of electrical energy stored by the battery means is less than about 10,000 Joules, and wherein the minimum lifespan of the device is less than about 3 years.

All existing ICD systems have single battery power systems that supply the initial minimum stored energy for the device. In a single battery system, even when no shocks are delivered, the number of remaining shocks in the device decreases with age due to the fact that the energy for the monitoring functions are drawn from this battery. To overcome this limitation, another embodiment of the present invention utilizes a dual battery power system with power for essentially all of the monitoring functions drawn from a first battery system and power for all output functions drawn from a second, and separate battery system. Assuming good charge retention of the second output battery system, essentially no energy is drawn from the output battery system until an electrical pulse therapy is delivered. Consequentially, one advantage of the dual battery system of this embodiment is that the minimum expected life span for the device is predictable, regardless of the number of initial shocks provided for by the device. This separation of battery functions allows for a further reduction in the overall size of the prophylactic ICD system having a fewer number of initial shocks provided for by the device.

Another enhancement to reduce the overall size of the battery means of the prophylactic ICD system is to increase the minimum charging time to about 15 seconds, as compared to about 10 seconds for the first embodiment of the present invention. This increase in minimum charging time, while not changing the overall stored energy requirements of the battery means of the prophylactic ICD system, does decrease the plate area required by the battery means due to the decrease in peak current requirement. This decrease in plate area translates into a decrease in the size of the battery means.

In addition to lowering the maximum stored energy for each charge and shortening the pulse duration to decrease the size of the capacitor and battery systems of the prophylactic ICD system of the present invention, the threshold detection criterion may also be modified to decrease the likelihood of false-positive shocks being delivered, particularly in the case of exercise induced sinus tachycardia. In one embodiment the initial detection criteria of the prophylactic ICD system is programmably established during implantation of the device at a heart rate well above the typical highest exercised-induced heart rate of the patient, e.g., 210 bpm or above. By using such a simple, but relatively fail-safe, initial detection criteria, the monitoring circuitry of the prophylactic ICD system can be simplified to further decrease the required size of the battery by reducing the steady state current drain of the device in its monitoring mode.

A still further enhancement of the prophylactic ICD system of the present invention is to operate the ICD device in an overcharged final countershock condition so as to provide greater efficacy and broader treatment modality for the device. Instead of delivering a repeated series of up to five countershocks at the maximum rated charging voltage in response to a persistent ventricular arrhythmia as is done in existing ICD systems, an overcharged final countershock is delivered for which the electrolytic capacitor charge storage system of the ICD system is charged at a voltage that exceeds a maximum voltage specification. By delivering an overcharged final countershock, the prophylactic ICD device can increase the chances of reversing a persistent ventricular arrhythmia which has become increasingly resistant to electrical therapy the longer the arrhythmia persists. As there is little to no risk in overcharging electrolytic capacitors for delivering the overcharged final countershock, and in fact the added electrical energy may overcome the increasing resistance to electrical countershock therapy, the present invention can deliver a more efficacious programmed therapy regimen than is available on existing ICD systems.

BRIEF DESCRIPTION OF THE DRAWING

FIGS. 4 and 5 are side and frontal plan views, respectively, showing the power, capacitor, circuit and connector ports means positioned in the preferred embodiment of the ICD system of FIG. 1.

DESCRIPTION OF THE PREFERRED EMBODIMENT

The function of the prophylactic ICD system of the present invention is to provide modest electrical treatment to a heart that is only mildly impaired, a form of therapy not available on this basis today because existing ICD systems are designed to provide therapies for patients with seriously abnormal heart conditions. As a result, existing ICD systems are poorly suited for protective or preventive applications in patients with mild heart conditions.

As used within the present invention, a mild or less severe cardiac condition can be specified, for example, in terms of the relative degree of cardiac output or ejection fraction of a patient's heart. Ejection fraction is the average proportion of blood in the left ventricle that is pumped out of the heart on each heart beat. Normal ejection fractions for people with healthy hearts can range from 60–80%, meaning that 60–80% of the blood in the left ventricle is pumped out of the heart on each heart beat. Mild or less severe cardiac conditions can be characterized by ejection fractions in a range from 40–60%, generally. Severe cardiac conditions can be characterized by ejection fractions in a range from 20–40%, and patients with ejection fractions of less than 20% are considered to have very severe cardiac conditions. While these ranges are good guidelines, it will be understood that the classification of a specific patient's cardiac condition is an individual matter to be performed by a trained cardiologist.

The prophylactic ICD system of the present invention includes an initial shock-delivery capability amounting to only about one-half to one-quarter as many shocks as existing ICD systems, with each shock delivered by the prophylactic ICD system requiring only one-quarter to three-quarters as much stored energy. Thus, the budgeted number of countershocks for the prophylactic ICD system will be less than about 200 countershocks, but more than about 100, with one embodiment having 150 budgeted countershocks. The stored energy requirements for each countershock will vary depending upon the embodiment described below. In general, the stored energy requirements for each countershock will be less than about 21 to 27 joules. In addition, the shocks delivered by a preferred embodiment of the prophylactic ICD system are biphasic shocks having a pulse duration as measured by the first phase of the biphasic shock that is shorter than typical in the existing ICD systems, and hence, is better tuned to the innate heart characteristic time.

Figure 1:
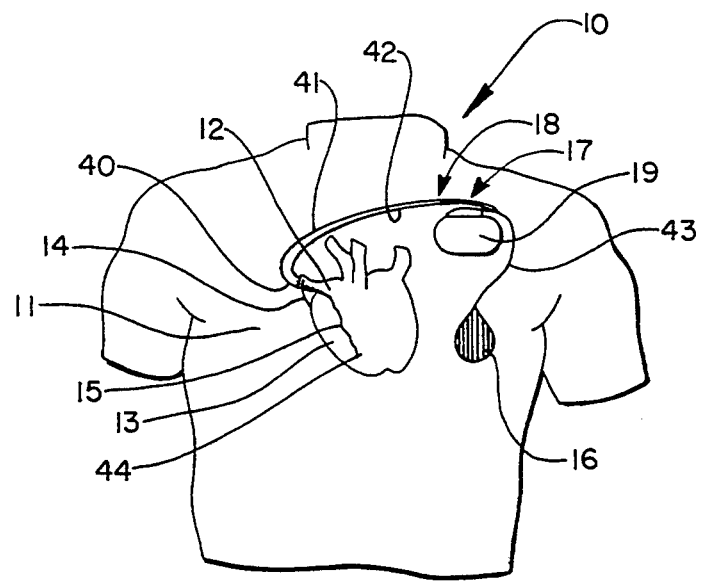
FIG. 1 is a frontal plan view showing a preferred embodiment of the prophylactic implantable cardioverter defibrillator (ICD) system of the present invention implanted in the pectoral position of a human patient.

FIG. 1 shows a preferred embodiment of a prophylactic ICD 17 of the present invention implanted in the pectoral region 18 of the chest 11 of patient 10. The prophylactic ICD 17 has a plurality of connector ports for connection to various implantable catheter and other electrode means, as is known in the art. For example, electrode leads 41 and 42 are shown extending form the prophylactic ICD 17 to catheter electrodes 40 and 15 which are passed, respectively, into the superior vena cava 14 and the right ventricle 13 of heart 12. Further, lead 43 is shown extending from the prophylactic ICD 17 to a subcutaneous patch electrode 16. The specific configuration of the electrodes of the defibrillation system is dependent upon the requirements of the patient as determined by the physician.

Figures 2, 3:
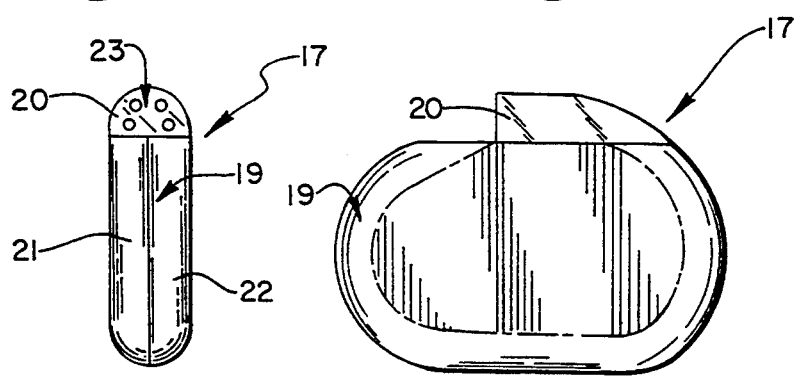
FIGS. 2 and 3 are frontal and side plan views, respectively, of the preferred embodiment of the prophylactic ICD system of FIG. 1.

FIGS. 2 and 3 show the prophylactic ICD 17 comprised of a housing 19 having mating half shells 21 and 22. Positioned and mounted on top of housing 19 is a top connector portion 20 having a plurality of connecting ports 23 which are described further below. Importantly, the prophylactic ICD 17 is comprised of a compact, self contained structure having predetermined dimensions which permits pectoral implantation. The housing 19 and top connector 20 are constructed and arranged to yield a cooperating structure which houses power means, control means and capacitive means. This cooperating structure permits subcutaneous implantation in the pectoral region of a human patient and provides a compact and effective ICD that automatically senses the bioelectrical signals of the heart and is able to provide a 750 volt capacitive discharge, for example, to the heart for defibrillation purposes.

It is important in this invention that the prophylactic ICD 17 be constructed and arranged to minimize the overall displacement volume of the device to allow for pectoral implantation, for example. The housing structure 19 is a compact and lightweight structure made of a biocompatable material and has a contoured configuration. The overall structure of this invention has a weight of less than 130 grams, and preferably less than 100–120 grams, and a volume of less than 90 cc, and preferably between about 40–80 cc.

As further shown in FIGS. 2 and 3, the housing structure 19 has a contoured periphery which is matingly connected to the top connector member 20 which also has a mating contoured configuration. The housing 19 is constructed of a biocompatable material such as a titanium or a stainless steel alloy. The top connector member 20 is also constructed of a biocompatable material, such as a biocompatable polymeric composition. It has further been found that for pectoral implantation purposes, that the housing structure 19 have a desired length to width to thickness ratio of approximately 5 to 3 to 1.

When the capacitor system of the first embodiment of the present invention is selected in accordance with the optimized minimum physiological current ($I_{pe}$) as described in the previously identified co-pending parent application entitled IMPLANTABLE CARDIOVERTER DEFIBRILLATOR HAVING A SMALLER DISPLACEMENT VOLUME, the capacitor system has an effective capacitance of approximately 85 $\mu$F, and is constructed and arranged to deliver an initial discharge voltage $V_d$ of 750 Volts, for example. The maximum stored electrical energy for a first arrangement of the ICD system is less than about 27 joules with an effective delivered defibrillation countershock energy of about 24–26 joules, depending upon the countershock waveform and electrodes through which the countershock is delivered. In the preferred embodiment, the effective discharge voltage and capacitance is achieved by using two flash-type capacitors in series, each having a capacitance rating of 170 $\mu$F and a voltage rating of 375 Volts, while occupying a total displacement volume of only 7 cc each. The output of the capacitors is in communication with an electronic circuitry output portion that generally is comprised of a flash type circuit which delivers the capacitor discharge through electrodes 15, 16 and 40, for example.

FIGS. 4 and 5 show the canister housing 19 having an interior space 30 wherein capacitors 26 and 27 are positioned and wherein a battery system 28 and circuit board portions 31 and 32 are positioned. The top connector 20 is shown mounted to the top of the canister housing 19. Connecting ports 36, 37 and 39 are shown positioned in the top connector 20. The connector ports 36 and 37 are connectible to the positive defibrillating electrode, for example, while connecting port 38 is connectible to the negative defibrillating electrode, for example, and the connecting port 39 receives the pacing/sensing electrode leads 41, 42. Channels 24 and 25 provide communicative and fastener members that provide for the attachment of the top connector 20 to the canister housing 19 and for the electrical connection between the ports 36, 37, 38 and 39 and the electronic elements positioned in the interior space 30 of housing 19.

As discussed, the top connector 20 of the defibrillator prophylactic ICD 17 has, for example, connecting ports 36 (DF+), 37(DF+), 38(DF-) and 39 (sensing/pacing). The lead connected to the DF- port, for example, is in conductive contact with the catheter electrode 15 placed in the right ventricle 13 of the heart 12. The electrode lead(s) connected to the DF+ port(s) are connected to either or both of the electrodes positioned in the superior vena cava 14 and the subcutaneous patch electrode 16. Alternatively, the DF+ port holes may not be utilized, and plugged by a stopper means, for example, when the ICD body itself is utilized as the positive element to complete the defibrillation circuit. The pacing/sensing electrode 44 provides an input to connecting port 39 of the prophylactic ICD 17 and provides continual monitoring of cardiac signals from the heart. The circuitry of the prophylactic ICD 17 has means to detect any tachycardiac or other arrhythmia condition and to thereby respond by the selective discharge of electrical energy stored in the capacitors 26 and 27.

Figure 6:
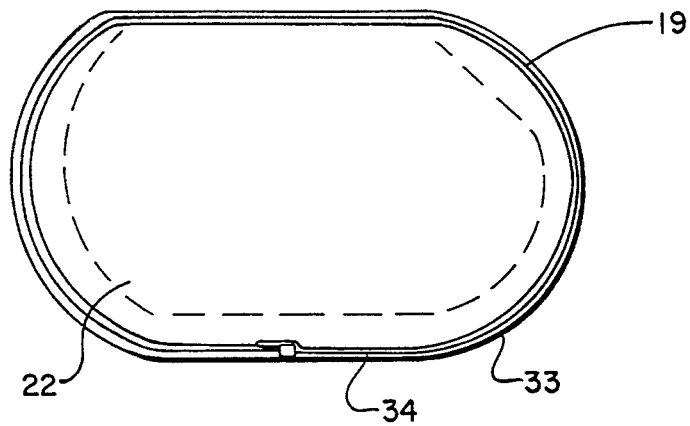
FIGS. 6 and 7 are plan views, showing the interior of the preferred embodiment of the ICD system of FIG. 1.
Figure 7:
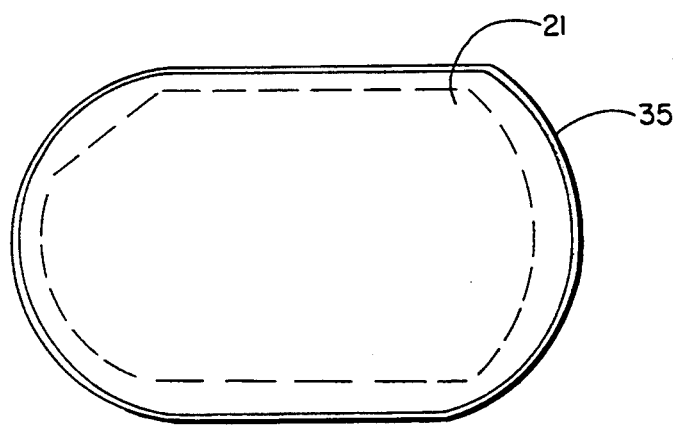

FIGS. 6 and 7 show the mating housing half shells 21 and 22, respectively of canister housing 19. The half shell 22 is shown to have an interior peripheral band 34 which is fixed adjacent the peripheral edge 33. The interior peripheral band 34 extends outwardly from the edge 33 of half shell 22 and is constructed and arranged to receive the peripheral edge 35 of housing half shell 21. Alternatively, the peripheral band 34 may be mounted within housing half shell 21, whereby the half shell 22 is positioned thereabout. The peripheral band 34 is also provided to shield the electronic components within housing 19 during the welding process uniting the body shells 21 and 22.

The flexible circuit board 29 is mounted within the interior space 30 of housing 19. The circuit board 29 provides for the sensing/pacing circuitry in communication with the lead extending from connecting port 39, for example. When a fibrillation episode is detected, the circuit board 29 causes the capacitors 26, 27 to discharge an initial 750 Volt charge through the electrode leads connected to ports 36-38, for example, and to the heart 12 of the patient 10. The electronic circuitry has a sensing portion which monitors the heart beat rate irregularity by means of two small electrodes 44, as is known in the art. In the preferred embodiment, the circuitry further has a processor portion which determines, with respect to a predetermined standard, when the output portion of the circuit will be activated.

By designing the prophylactic ICD system to have these different characteristics than existing ICD systems, the prophylactic ICD system can be also be packaged in an ICD package that is smaller than about 75 cc, and preferably smaller than about 50-60 cc. The smaller size of the prophylactic ICD system of the present invention permits implantation of the ICD package in the pectoral region of a human patient, where its housing can serve advantageously as an electrode for shock delivery. In addition, the prophylactic ICD system is highly compatible with a conventional catheter cardioversion-defibrillation electrode, and thus avoids the need for thoracic surgery altogether.

An additional feature of this and other embodiments of the present invention is to use an overcharged final countershock feature as described in more detail in the previously identified co-pending application entitled OVERCHARGED FINAL COUNTERSHOCK FOR AN IMPLANTABLE DEFIBRILLATOR. Due to the fact that electrolytic capacitors can be overcharged from 5% to 15% above the rated maximum voltage for the capacitor before the leaking current begins to exceed the charging current, the possible increase in countershock energy to be gained can be 10% to 25%, as the energy of the delivered countershock is a function of the square of the charging voltage. As a result, the delivered energy for the final countershocks to be delivered as part of a programmable therapy regimum of multiple countershocks in response to a persistent cadiac arrhythmia can be boosted by this amount in the prophylactic ICD system, or the ICD system size can be reduced by this amount, or the benefit can be shared between energy used and volume displaced.

While it would appear that using an overcharged final countershock might decrease, rather than increase, the ultimate safety and efficacy of an ICD device by operating the capacitor charging system beyond its maximum rated voltages, this is not the case. On the contrary, this embodiment takes advantage of the fact that the nature of electrolytic capacitors is not to fail catastrophically when charged beyond standard ratings. Typically, electrolytic capacitors have a maximum rated charging voltage below which leakage current is nominal. Beyond the maximum rated charging voltage, leakage current grows with increasing charging voltage. Unlike other types of capacitor technologies, however, there is no breakdown of the capacitor when it is charged above its maximum charging voltage. Instead, when the leakage current equals the charging current the electrolytic capacitor will not charge any further, but will remain in a steady state condition balancing the leakage current with the charging current.

There are several ways to monitor charging of the capacitor system in preparation for delivering an overcharged final countershock. One method simply specifies a charging time based on accurate knowledge of the capacitor properties. Another monitors the monotonically declining first derivative of the capacitor voltage, ending the charging cycle when the derivative has dropped to some preset value. A different method interrupts charging briefly and periodically to observe the leakage phenomenon by observing capacitor voltage decline. Still another method measures capacitor leakage directly by measuring voltage across a resistor connected between the capacitor and ground. Yet another approach is to simply program the ICD system to charge at an unconventionally high voltage, for example 800 volts or more, that is above the maximum programmable voltage of the device.

In the case of a prophylactic ICD system operating in an overcharged final countershock mode where the ICD system is charged to 800 volts on the final countershock, for example, there would be about a 12% increase in the stored energy for that final countershock. This extra energy may significantly improve the chances that the final countershock would be more productive than the preceeding countershocks which were unable to convert the cardiac arrhthmia.

Another embodiment of the prophylactic ICD system of the present invention takes advantages of the appropriateness of lower-energy treatments for patients with less severe cardiac conditions. This embodiment of the present invention assumes that relatively healthier hearts will require less energy for defibrillation than do hearts with more serious deficiencies. Consequently, this embodiment further decrease the maximum stored energy required of the ICD system to less than about 21 Joules, while retaining the shorter duration biphasic countershock waveform. When combined with a total budgeted number of countershocks of less than about 200, the result is a still further decrease in the overall size and stored energy requirements of the ICD system such that this embodiment of the prophylactic ICD system requires less than about 7000 Joules of stored energy for countershock delivery.

In accordance with this embodiment, the maximum stored energy required for the ICD system is decreased from about 27 joules to about 21 joules, decreasing the effective delivered energy from between about 24-26 joules to between about 17-20 joules. While this decreased maximum energy might not be capable of providing an adequate safety margin for patients having ejection fractions less than 20%, it does provide an adequate safety margin for patients with less severe cardiac conditions (i.e., patients with ejection fractions generally greater than about 20%) within a minimum defibrillation threshold for that patient as determined by the physician or cardiologist at the time the ICD system is to be implanted.

In this embodiment, the stored energy requirements for a battery and capacitor system are reduced by about one-quarter from that of the first embodiment, thereby resulting in a further decrease of up to 25% in the size of the battery source which provides the stored energy for the countershocks, provided that the minimum number of budgeted countershocks is greater than about 100. In this case, the size of the battery source for providing the stored energy for the countershocks is less than about 7000 joules and is preferably less than about 5000 joules. In this embodiment, it should be understood that the size of the battery source for providing the stored energy for the countershocks is calculated separate from the energy requirements for monitoring and/or pacing, for example. In any event, the total energy requirements for the battery system of this second embodiment is less than 12,000 joules, and preferably less than about 10,000 joules.

Another feature of the embodiment having maximum stored energy for each countershock of less than about 21 joules is that the effective capacitance of the capacitor system required to deliver this energy may be less than the 85 $\mu f$ effective capacitance of the ICD system of the first embodiment. In one example, a pair of photoflash electrolytic capacitors 26 and 27 each having capacitance values of 130 $\mu f$ are used to produce a total effective capacitance of 65 $\mu f$ and a time constant, tau, of about 3.25 ms, while requiring up to 25% less space than the pair of 170 $\mu f$ electrolytic capacitors 26 and 27 shown in the first embodiment. Despite using the lower effective capacitance values, it is still possible to achieve a physiologically effective current of about 5.0 Amps, for example, for a monophasic countershock. This is possible because a smaller effective capacitance value is more efficient at delivering its charge to the heart and, hence, the resulting physiologically effective current does not decrease linearly with a decrease in effective capacitance.

Still another embodiment of the present invention takes advantage of shortening the minimum lifespan of the device to further decrease the overall size and stored energy requirements of the prophylactic ICD system. Decreased cardiac output or ejection fraction can be caused by any number of conditions. In the case of mild cardiac conditions, a decreased ejection fraction is typical after a patient experiences a heart attack or myocardial infarction. Clinical experience has shown that there is about a 10% probability that a patient will experience a fibrillation episode within the first 12–24 months after a heart attack, but that the incidence of fibrillation in decreases significantly after this period. Bigger, et al., "The Relationship Among Ventricular Arrhythmia, Left Ventricular Dysfunction and Mortality in the Two Years After Myocardial Infarction", Circulation, Vol. 69:250 (1984). In other words, if a patient can survive the first two years after a heart attack, the likelihood of another heart attack or fibrillation due to the original condition is very small. When coupled with the rationale for a prophylactic ICD system discussed in the background art section, this data suggests that there is merit in providing a prophylactic ICD system having a minimum expected lifespan of less than about 3 years, rather than the conventional minimum lifespan of existing ICD systems which is set at 5 years.

In the first embodiment previously described, the idle current or current necessary to operate the monitoring mode is about 10 $\mu A$ at about 3 V, or about 30 $\mu$watts of power drain. If the minimum lifespan of the device is 5 years, then the idle current alone requires the device to provide 30 $\mu$watts times 31.5 million seconds/year or about 1000 joules for each year of lifespan of the device. Thus, by decreasing the minimum lifespan of the device by 2 years or 40%, the resulting energy savings in reduced monitoring energy requirements is almost 2000 joules. When the reduced minimum lifespan of the device is combined with the reduced maximum stored energy requirements as previously discussed, the total energy requirements for the prophylactic ICD system are even further decreased to a total energy requirement, including both required shock energy and required monitoring energy, of less than about 8000 joules, and preferably less than about 7000 joules. This results in a net energy saving of almost 50% as compared to the total energy requirements for existing ICD systems of almost 15,000 joules.

Figure 8:
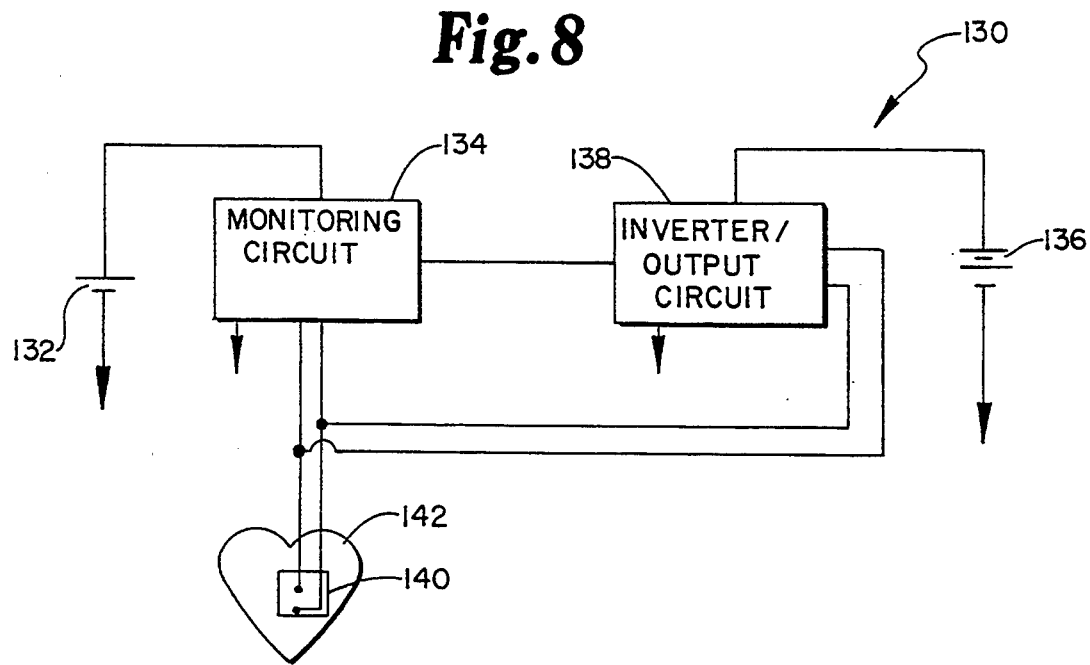
FIG. 8 shows an electrical schematic of a dual battery embodiment of the present invention.

FIG. 8 illustrates a block diagram of the dual battery system 130 for an implantable defibrillator of this embodiment of the present invention. A battery 132 of appropriate voltage and physical size connects to and powers a monitoring circuit 134 only. Another battery 136 of appropriate voltage and physical size connects to and powers the inverter/output circuit 138 only. The monitoring circuit 134 and the inverter/output circuit 138 each connect to two or more implanted electrodes 140 on, near or in a heart 142. The monitoring circuit 134 also connects to and triggers the inverter/output circuit 138. The batteries 132 and 136 are optimally sized electrically and physically to provide for the most efficient operation for their respective circuitry.

In operation, the implantable cardioverter defibrillator shown in FIG. 8 is dependent upon the monitoring circuit 134 and the inverter/output circuit 138. In the event that the monitoring circuit 134 detects a wake-up condition, for example, the monitoring circuit 134 wakes up a microprocessor-based circuit in the inverter/output circuit 138 to respond to the wake-up condition. In the event that the monitoring circuit 134 is programmably enabled for pacing detection, and the monitoring circuit 134 detects a pacing condition, the monitoring circuit enables a hardware-based pacing circuit portion of the inverter/output circuit 138 to deliver a pacing pulse using energy from the battery 136.

It will be noted that many different variations in conditions detected by the monitoring circuit 134 and types of responses provided by the inverter/output circuit 138 are possible, and it is intended that such combinations are within the scope of the present invention. In a preferred embodiment, a microprocessor with an RC gated oscillator circuit that is controlled by the microprocessor within the inverter/output circuit 138 implements a wake-up control that can respond to the wake-up conditions. The wake-up conditions handled by the microprocessor based circuit in the inverter/output circuit 138 include, for example, a simplified defibrillation threshold determination, a telemetry indication, or a timer condition. In the case of the defibrillation threshold determination, for example, threshold determination circuitry in the monitoring circuit 134 detects the occurrence of a heart rate well above the typical highest exercised-induced heart rate of the patient, e.g., 210 bpm or above. In response, the monitoring circuit 134 wakesup the microprocessor in the inverter/output circuit 138, which verifies that a cardiac arrhythmia is occurring and selects an appropriate electrical pulse therapy. If an electrical pulse therapy is to be delivered, the battery 136 would charge the inverter/output circuit 138 to deliver one or more high voltage cardioversion/defibrillation countershocks. By using such a simple, but relatively fail-safe, initial detection criteria, the monitoring circuitry of the prophylactic ICD system can be simplified to further decrease the required size of the battery by reducing the steady state current drain of the device in its monitoring mode.

If the wake-up condition was a telemetry indication, then the microprocessor circuit of the inverter/output circuit 138 might output a telemetry response, for example, rather than an electrical pulse therapy response. Alternatively, if the microprocessor circuit of the inverter/output circuit 138 determines that no action is required in response to the wake-up condition, then no "output" may be generated in response and the microprocessor would turn off the RC gated oscillator circuit, thereby shutting off the clock to the microprocessor.

One important feature which distinguishes the dual battery system 130 from the previous attempts to implement dual battery systems is that the division of labor between the battery 132 and the battery 136 is not based on low voltage output vs. high voltage output, but rather is based on monitoring functions vs. output functions. In the two dual battery systems described in the background art section, all of the low voltage circuitry of the implantable cardioverter defibrillator was powered from a low voltage battery. As a result, both the monitoring function (which typically operate on 3V levels), as well as the pacing therapy output functions (which typically operate on 6V levels), were designed to derive their energy from the low voltage battery. The end result of this type of arrangement is that the life of the low voltage battery is totally dependant upon the amount of pacing therapy which may be delivered by the device and, thus, the minimum effective life of the device is effectively unknown.

In contrast, the improved dual battery power system of the present invention takes all of its "output" energy from the output battery 132. For example, the present invention does not take the energy for pacing therapy from the monitoring battery 132, but rather from the output battery 136. As a result, the monitoring lifespan of an implantable defibrillator in accordance with the present invention is known and calculable based on the specifications of the monitoring battery 132. Without a known lifespan of the device, it is simply not possible to provide a viable implantable defibrillator, as evidenced by the fact that both of the previous attempts at dual battery systems which did not have known lifespans for the monitoring circuitry were unsuccessful and did not result in manufactured implantable cardioverter defibrillators. For a more detailed explanation of the operation of the dual battery implementation of the present invention, reference is made to the previously identified co-pending application entitled IMPROVED DUAL BATTERY POWER SUPPLY FOR AN IMPLANTABLE CARDIOVERTER DEFIBRILLATOR.

In addition to the dual battery implementation, this embodiment also increases the charging time for the ICD system, thereby decreasing the peak effective current which must be delivered by the output battery 136. The charging time for the capacitors 26 and 27 are governed by the following equation:

$$E_{max} = (e * V_b * I_b) * t$$

where t is the charging time at the point the ICD is implanted for the maximum energy stored, $E_{max}$. $V_b$ and $I_b$ are the voltage and current draws which the battery 136 is capable of providing and e is the charging efficiency of the transformer circuit of the ICD system. In this example, a minimum worst-case $V_b$ is assumed to be about 4.5V at the end life of the 6V battery 136 and the charging efficiency is about 50%. Under these conditions, if the battery 136 is capable of delivering a minimum worst-case 1 Amp peak current, the maximum worst-case charging time would be about 10 seconds for a $E_{max}$ of less than about 21 joules. If the maximum worst-case charging time is allowed to rise to 15 seconds, the peak current requirement of the battery 136 would drop to about 0.65 A.

In the first embodiment previously described, the peak current requirement of the battery is about 3.0 A in order to charge a $E_{max}$ of about 27 joules in less than about 10 seconds. Because the plate area of the battery system is a function of the peak current, a decrease of 67% or more as compared to the first embodiment can result in a significant decrease of the size of the battery 136 of up to 50% as compared with the first embodiment of the present invention. When the decrease in the peak current requirements of battery 136 are coupled with the corresponding decreases in the requirements for battery 138 because of 10–50% in the idle current draw due to the simplified monitoring circuitry, the overall size of the battery system for this embodiment of the ICD system of the present invention is significantly decreased.

As an example of how an optimized battery budget might look for an ICD system in accordance with this embodiment, consider the following example for a prophylactic ICD system with a budgeted number of countershocks of 150, a peak current requirement of 0.75 A and a minimum lifespan for the device of about 3 years with no pacing capabilities. The total energy required in terms of Amp-hours for each battery 136 and 138 can be calculated as follows:

$$\begin{aligned} E_{t-136} &= (I_b * t) * N_p \\ &\quad (.75\,A * 12.5\,\text{sec}) * 150 \\ &\quad .4\,A\ \text{hours} \end{aligned}$$

$$\begin{aligned} E_{t-138} &= (I_i * 1) \\ &\quad 8\,\mu A * 3\ \text{years} \\ &\quad .2\,A\ \text{hours} \end{aligned}$$

In this embodiment, the total battery budget is less than 0.6 Ahours or 70% less than the total battery budget of about 2.0 Ahours for the first embodiment previously described. Even assuming a device that also stored enough pacing energy to providing pacing pulses for up to 1 year, a requirement that would add about 0.3 Ahours of energy to the total battery budget, no reduction in the idle current draw of 10 μA, and a minimum budgeted number of countershocks of 200, the total battery budget of a prophylactic ICD system having the dual battery and decreased maximum shock energy storage embodiments is still less than about 1.2 Ahours, or about 40% less than the first embodiment previously described.

We claim:

1. A prophylactic implantable cardioverter defibrillator device for subcutaneous positioning within a pectoral region of a human patient capable of internally storing sufficient electrical energy so as to effectively treat a mildly impaired cardiac dysrhythmia condition comprising:

a sealed housing structure, having at least two walls defining an interior space therebetween the at least two walls, constructed of a biocompatible material and having a displacement volume of less than about 75 cc and including one or more connector ports disposed in a wall of said structure for providing electrical connections between said interior space of said structure and electrode leads in said patient;

circuit means, within said interior space, including:
means for sensing cardiac signals received from said electrode leads;
means for detecting and confirming a dysrhythmia in said cardiac signals; and
means for controlling delivery of one or more electrical cardioversion/defibrillation countershocks of at least 0.5 Joules to said patient in response to the detection of a dysrhythmia;

capacitor means within said interior space for storing electrical energy to generate said electrical cardioversion/defibrillation countershocks and having an effective capacitance of less than about 100 µF; and battery means within said interior space for providing electrical energy to said circuit means and said capacitor means and capable of charging said capacitor means to a maximum stored electrical charge energy of less than about 27 Joules, wherein a total amount of electrical energy stored by said battery means is less than about 12,000 Joules and a budgeted number of electrical cardioversion/defibrillation countershocks is greater than about 100 and less than about 200.

2. The device of claim 1 wherein said means for controlling delivery of defibrillation countershocks includes an inverter/output circuit to produce electrical cardioversion/defibrilation waveforms which are biphasic.

3. The device of claim 1 wherein said battery means comprises:
first battery means for providing electrical power primarily only to the circuit means for sensing cardiac conditions; and
second battery means for providing substantially all of the electrical power for charging said capacitor means.

4. The device of claim 1 wherein said battery means has a worst-case minimum charging time for charging said capacitor means to said maximum stored electrical charge that is less than about 10 seconds.

5. The device of claim 1 wherein:
said means for detecting and confirming is programmable to reconfirm a detection of a dysrhythmia following delivery of at least one countershock: and the circuit means further includes:
means for storing a programmable therapy regimen;
means for regulating a charging voltage applied by the battery means to the capacitor means in response to a charging voltage value indicated in the programmable therapy regimen;
means for selectively discharging the capacitor means as an electrical countershock in response to a reconfirmed detection of the dysrhythmia;
means for counting a successive number of failed electrical countershocks in the programmable therapy regimen when the electrical countershock was not successful in treating the dysrhythmia; and
means for resetting the means for counting to zero after a successful treatment of a myocardial fibrillation,
wherein at least one of the charging voltage values in the programmable therapy regimen is a maximum nominal voltage and at least another of the charging voltage values in the programmable therapy regimen is an overcharged voltage greater than the maximum voltage.

6. The device of claim 5 wherein the capacitor means is a pair of electrolytic capacitors in series and the electrolytic capacitors maximal nominal voltage is at least 750 volts such that there is a maximum charging voltage value of not greater than 375 volts across each capacitor.

7. A prophylactic implantable cardioverter defibrillator device for subcutaneous positioning within a pectoral region of a human patient capable of internally storing sufficient electrical energy so as to effectively treat mildly impaired cardiac dysrhythmia conditions comprising:
a sealed housing structure, having at least two walls defining an interior space there between the at least two walls, constructed of a biocompatible material and having a displacement volume of less than about cc and including one or more connector ports disposed in a wall of said structure for providing electrical connections between said interior space of said structure and electrode leads in said patient;
circuit means, within said interior space, including:
means for sensing cardiac signals received from said electrode leads;
means for detecting and confirming a dysrhythmia in said cardiac signals; and
means for controlling delivery of one or more electrical cardioversion/defibrillation countershocks of at least 0.5 Joules to said patient in response to the detection of a dysrhythmia;
capacitor means within said interior space for storing electrical energy to generate said electrical cardioversion/defibrillation countershocks and having an effective capacitance of less than about 100 µF; and
battery means within said interior space for providing electrical energy to said circuit means and said capacitor means and capable of charging said capacitor means to a maximum stored electrical charge energy of less than about 21 Joules,
wherein an amount of electrical energy stored by said battery means to provide said electrical cardioversion/defibrillation countershocks is less than about 7500 Joules and a budgeted number of electrical cardioversion/defibrillation countershocks is greater than about 100 and less than about 200.

8. The device of claim 7 wherein said means for controlling delivery of defibrillation countershocks includes an inverter/output circuit to produce electrical cardioversion/defibrillation waveforms which are biphasic.

9. The device of claim 7 wherein said battery means comprises:
first battery means for providing electrical power primarily only to the circuit means for sensing cardiac conditions; and
second battery means for providing substantially all of the electrical power for charging said capacitor means.

10. The device of claim 7 wherein said battery means has a worst-case minimum charging time for charging said capacitor means to said maximum stored electrical charge that is at least about 10 seconds and less than about 15seconds.

11. The device of claim 7 wherein said circuit means comprises:

wake-up circuit means that responds to one or more wake-up conditions for the device selected from the group Of wake-up conditions consisting of: detecting a dysrhythmia, detecting a wake-up signal external to the device, detecting a low power condition for the device, and detecting a failure condition for the device; and microprocessor circuit means that is powered up in response to a signal from said wake-up circuit means to process said wake-up condition.

12. The device of claim 11 wherein said wake-up circuit means detects said arrhythmia by detecting whether said cardiac signals represent a heart beat of greater than about 210 bpm, such that said wake-up circuit means has an idle current requirement that is less than about 10 $\mu A$.

13. The device of claim 7 wherein said effective capacitance value of said capacitor means is between about 40 $\mu f$ and 70 $\mu f$.

14. The device of claim 7 wherein:

said means for detecting and confirming is programmable to reconfirm a detection of a..dysrhythmia following delivery of at least one countershock; and the circuit means further includes:

means for storing a programmable therapy regimen:

means for regulating a charging voltage applied by the battery means to the capacitor means in response to a charging voltage value indicated in the programmable therapy regimen;

means for selectively discharging the capacitor means stored electrical energy as an electrical countershock in response to a reconfirmed detection of the dysrhythmia;

means for counting a successive number of failed electrical countershocks in the programmable therapy regimen when the electrical countershock was not successful in treating the dysrhythmia; and means for resetting the means for counting to zero after a successful treatment of a myocardial fibrillation, wherein at least one of the charging voltage values in the programmable therapy regimen is a maximum nominal voltage and at least another of the charging voltage values in the programmable therapy regimen is an overcharged voltage greater than the maximum nominal voltage.

15. The device of claim 14 wherein the capacitor means is a pair of electrolytic capacitors in series and the electrolytic capacitors maximal nominal voltage is at least 750 volts such that there is a maximum charging voltage valise of greater than 375 volts across each capacitor.

16. A prophylactic implantable cardioverter defibrillator device for subcutaneous positioning within a pectoral region of a human patient capable of internally storing sufficient electrical energy so as to effectively treat mildly impaired cardiac dysrhythmia conditions comprising:

a sealed housing structure, having at least two walls defining an interior space the at least two walls, constructed of a biocompatible material and having a displacement volume of less than about 60 cc and including one or more connector ports disposed in a wall of said structure for providing electrical connections between said interior space of said structure and electrode leads in said patient;

circuit means, within said interior space, including:

means for sensing cardiac signals received from said electrode leads;

means for detecting and confirming a dysrhythmia in said cardiac signals; and means for controlling delivery of one or more electrical cardioversion/defibrillation countershocks of at least 0.5 Joules to said patient in response to the detection of a dysrhythmia;

capacitor means within said interior space for storing electrical energy to generate said electrical cardioversion/defibrillation countershocks and having an effective capacitance of less than about 100 $\mu F$; and battery means within said interior space for providing electrical energy to said circuit means and said capacitor means and capable of charging said capacitor means to a maximum stored electrical charge energy of less than about 21 Joules, wherein a total amount of electrical energy stored by said battery means is less than about 10000 Joules, a budgeted number of electrical cardioversion/defibrillation countershocks is greater than about 100 and less than about 200, and the minimum lifespan of the device is less than about 3 years.

17. The device of claim 16 wherein said means for controlling delivery of defibrillation countershocks includes an inverter/output circuit to produce electrical cardioversion/defibrillation waveforms which are biphasic.

18. The device of claim 16 wherein said battery means comprises:

first battery means for providing electrical power primarily only to the circuit means for sensing cardiac conditions; and second battery means for providing substantially all of the electrical power for charging said capacitor means.

19. The device of claim 16 wherein said battery means has a worst-case minimum charging time for charging said capacitor means to said maximum stored electrical charge that is at least about 10 seconds and less than about 15 seconds.

20. The device of claim 16 wherein said circuit means comprises:

wake-up circuit means that responds to one or more wake-up conditions for the device selected from the group of wake-up conditions consisting of: detecting a dysrhythmia, detecting a wake-up signal external to the device, detecting a low power condition for the device, and detecting a failure condition for the device; and microprocessor circuit means that is powered up in response to a signal from said wake-up circuit means to process said wake-up condition.

21. The device of claim 20 wherein said wake-up circuit means detects said arrhythmia by detecting whether said cardiac signals represent a heart beat of greater than about 210 bpm, such that said wake-up circuit means has an idle current requirement that is less than about 10 $\mu A$.

22. The device of claim 16 wherein said effective capacitance value of said capacitor means is between about 40 $\mu f$ and 70 $\mu f$.

23. The device of claim 16 wherein:

said means for detecting and confirming is programmable to reconfirm a detection of dysrhythmia following delivery of at least one countershock; and the circuit means further includes:
- means for storing a programmable therapy regimen;
- means for regulating a charging voltage applied by the battery means to the capacitor means in response to a charging voltage value indicated in a programmable therapy regimen;
- means for selectively discharging the capacitor means stored electrical energy as an electrical countershock in response to a reconfirmed detection of the dysrhythmia;
- means for counting a successive number of failed electrical countershocks in the programmable therapy regimen when the electrical countershock was not successful in treating the dysrhythmia; and
- means for resetting the means for counting to zero after a successful treatment of a myocardial fibrillation, wherein at least one of the charging voltage values in the programmable therapy regimen is a maximum nominal voltage and at least another of the charging voltage values in the programmable therapy regimen is an overcharged voltage greater than the maximum voltage.

24. The device of claim 23 wherein the capacitor means is a pair of electrolytic capacitors in series and the electrolytic capacitors maximal nominal voltage is at least 750 volts such that there is a maximum charging voltage value of greater than 375 volts across each capacitor.

* * * * *